US010565399B2

(12) United States Patent
Huang

(10) Patent No.: US 10,565,399 B2
(45) Date of Patent: Feb. 18, 2020

(54) BOTTOM UP DATA ANONYMIZATION IN AN IN-MEMORY DATABASE

(71) Applicant: SAP SE, Walldorf (DE)

(72) Inventor: Xinrong Huang, Shanghai (CN)

(73) Assignee: SAP SE, Walldorf (DE)

( * ) Notice: Subject to any disclaimer, the term of this patent is extended or adjusted under 35 U.S.C. 154(b) by 169 days.

(21) Appl. No.: 15/794,779

(22) Filed: Oct. 26, 2017

(65) Prior Publication Data
US 2019/0130130 A1    May 2, 2019

(51) Int. Cl.
G06F 21/62 (2013.01)
G06K 9/62 (2006.01)
G16H 10/60 (2018.01)
G06F 16/28 (2019.01)
G06F 16/2457 (2019.01)

(52) U.S. Cl.
CPC .... *G06F 21/6254* (2013.01); *G06F 16/24578* (2019.01); *G06F 16/285* (2019.01); *G06K 9/6218* (2013.01); *G16H 10/60* (2018.01); *H04L 2209/42* (2013.01)

(58) Field of Classification Search
CPC .............. G06F 21/6254; G06F 16/285; G06F 16/24578; G16H 10/60; G06K 9/6218; H04L 2209/42
See application file for complete search history.

(56) References Cited

U.S. PATENT DOCUMENTS

| | | | |
|---|---|---|---|
| 2011/0321169 A1 | 12/2011 | Cormode et al. | |
| 2013/0198194 A1 | 8/2013 | Chen et al. | |
| 2014/0380498 A1* | 12/2014 | Toyoda | G06F 21/6254 726/27 |
| 2015/0033356 A1* | 1/2015 | Takenouchi | H04L 63/0407 726/26 |
| 2015/0254462 A1* | 9/2015 | Takahashi | G06F 21/60 726/26 |

FOREIGN PATENT DOCUMENTS

JP  2012-003440 A  1/2012

OTHER PUBLICATIONS

Jian Xu, Wei Wang, Jian Pei, Xiaoyuan Wang, Baile Shi, Ada Wai-Chee Fu 'UtilityBased Anonymization for Privacy Preservation with Less Information Loss' ACM SIGKDD Explorations Newsletter, vol. 8 Issue 2, Dec. 2006, pp. 21-30 (Year: 2006).*

(Continued)

*Primary Examiner* — Catherine Thiaw
(74) *Attorney, Agent, or Firm* — Sterne, Kessler, Goldstein & Fox P.L.L.C.

(57) ABSTRACT

Disclosed herein are system, method, and computer program product embodiments for data anonymization in an in-memory database. An embodiment operates by receiving an indication to perform data anonymization based on one or more quasi attributes of a data set. The data set is sorted based on the one or more quasi attributes. The sorted data set is grouped into a first plurality of groups. A particular group that does not include enough records to satisfy an anonymization threshold is identified from amongst the first plurality of groups. The particular group is combined with another group of the first plurality of groups.

17 Claims, 5 Drawing Sheets

(56) References Cited

OTHER PUBLICATIONS

Md. Enamul Kabir • Hua Wang • Elisa Bertino 'Efficient systematic clustering method for k-anonymization', Acta Informatica (2011) 48:51-66 (Year: 2011).*
Extended European Search Report, dated Oct. 11, 2018, for European Patent Appl. No. 18184495.2, 10 pages.
Lefevre, K. et al., "Mondrian Multidimensional K-Anonymity," *Proceedings of the 22nd International Conference on Data Engineering*, 11 pages (2006).
Lefevre, K. et al., "Workload-Aware Anonymization," *Proceedings of KDD*, pp. 277-286 (Aug. 20-23, 2006).
Li, N. et al., "t-Closeness: Privacy Beyond k-Anonymity and l-Diversity," *Proceedings of the 23rd IEEE International Conference on Data Engineering*, pp. 106-115 (2007).
Machanavajjhala, A. et al., "l-Diversity: Privacy Beyond k-Anonymity," *ACM Transactions on Knowledge Discovery from Data*, vol. 1, No. 1, Article 3, 52 pages (Mar. 2007).
Sweeney, L., "k-Anonymity: A Model for Protecting Privacy," *International Journal on Uncertainty, Fuzziness and Knowledge-based Systems*, vol. 10, No. 5, pp. 557-570 (2002).
Xu, J. et al., "Utility-Based Anonymization Using Local Recoding," *Proceedings of the 12th ACM SIGKDD International Conference on Knowledge Discovery and Data Mining*, pp. 785-790, New York, NY, USA (Aug. 20-23, 2006).

\* cited by examiner

BOTTOM UP DATA ANONYMIZATION IN AN IN-MEMORY DATABASE

CROSS REFERENCE TO RELATED APPLICATIONS BRIEF DESCRIPTION OF THE DRAWINGS

This application is related to U.S. patent application Ser. No. 15/794,807, filed herewith, entitled "Data Anonymization In An In-Memory Database,", and U.S. patent application Ser. No. 15/794,744, filed herewith, entitled "K-Anonymity and L-Diversity Data Anonymization In An In-Memory Database,", all of which are hereby incorporated by reference in their entireties.

BACKGROUND

Data anonymization is a data privacy technique in which personal information from data of a database is protected via deletion or encryption such that individuals about whom the information relates cannot be identified. Data anonymization may be used to protect the privacy of individuals or companies about whom data has been collected while at the same time maintaining the integrity of the released data that is being shared. Current techniques being used to anonymize data typically apply to numerical data or hierarchical data and cannot be applied to other types of data, such as textual data, thus limiting the anonymization options that are available. In order to protect from the disclosure of individual or sensitive information, data may be lost during the anonymization process. For this reason, users often will want to balance protecting individual or sensitive data with minimizing information loss.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Provided herein are system, apparatus, device, method and/or computer program product embodiments, and/or combinations and sub-combinations thereof, for data anonymization in an in-memory database.

Figure 1:
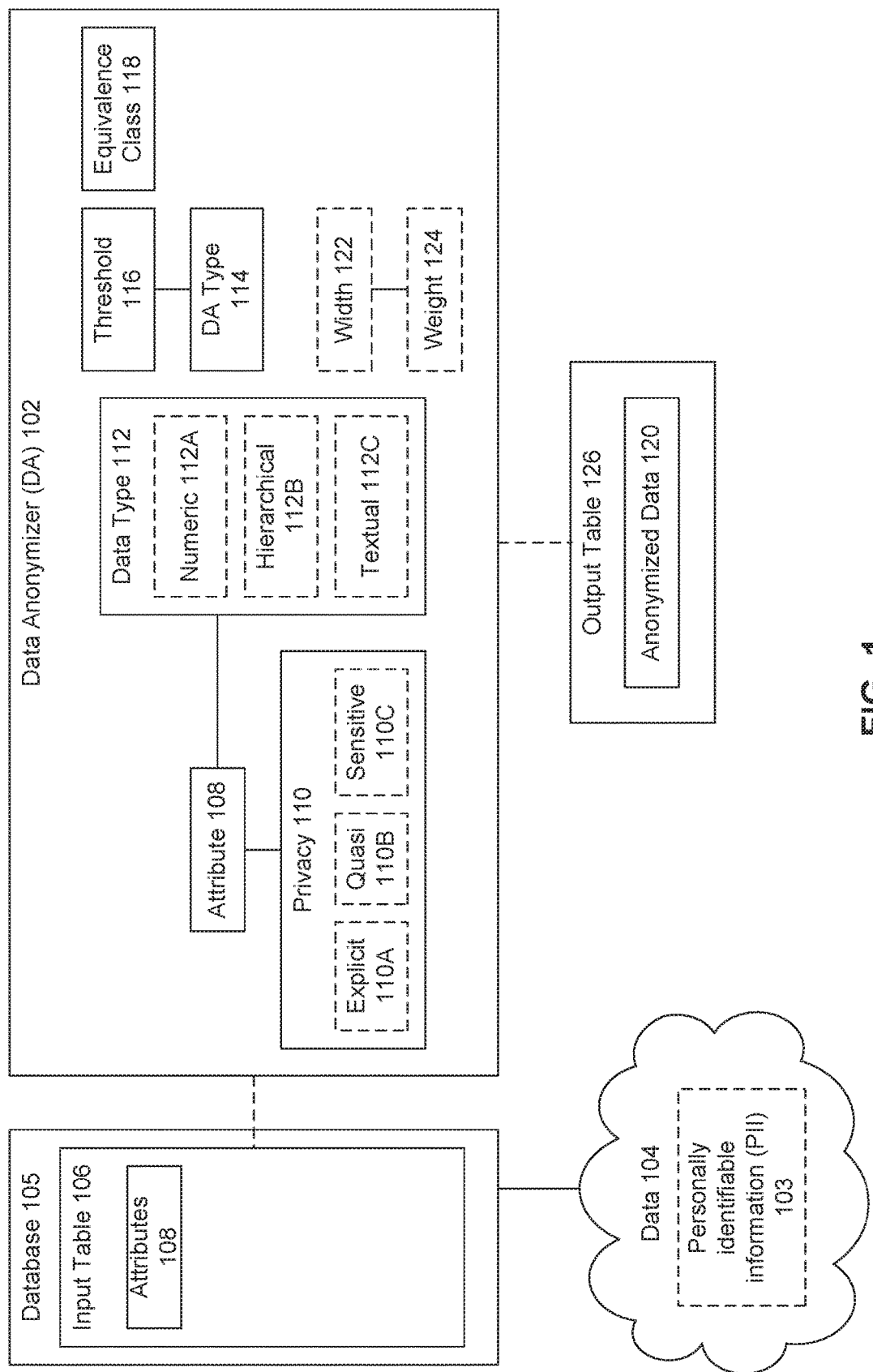
FIG. 1 is a block diagram illustrating example data anonymization functionality in an in-memory database, according to some embodiments.

FIG. 1 is a block diagram 100 illustrating example data anonymization functionality in an in-memory database, according to some embodiments. Data Anonymizer (DA) 102 may use data anonymization to protect the privacy or identity of individuals about whom data 104 has been collected and is being published or otherwise made publicly available. DA 102 may further avoid the disclosure of sensitive information.

In some embodiments, DA 102 may use various data anonymization techniques that delete, encrypt, or otherwise obscure personally identifiable information (PII) 103 within data 104 while maintaining as much of the remaining data as possible. PII 103 may include any data values, objects or types that may be used to identify or potentially identify particular individuals or companies about whom data 104 was collected. DA 102 may enable data 104 about individuals to be publicly released, while not releasing enough information to be able to identify the actual individuals about whom the data pertains.

For example, data 104 may have been collected from individuals for the purposes of medical or market research. The data 104 may include PII 103 that is useful for identifying the individuals and may have been used to test a hypothesis, conduct experiments, or perform studies. In an embodiment, the results of data analysis may be published in a journal or online, presented at a conference, or otherwise made publicly available. To support the results, portions of the data 104 used in the studies may be released as well. However, what is often unnecessary (and what may be desired to be avoided) is to release the specific identities of the individuals about whom the data 104 was collected.

DA 102 may anonymize portions of data 104 to remove or otherwise obscure PII 103 such that it is difficult or impossible to specifically identify an individual about whom the released anonymized data 120 pertains. With expanded anonymization techniques, as being applied to different data types 112, DA 102 may perform the minimum amount of anonymization necessary to protect the privacy of individuals while maintaining as much of the integrity of the remaining data 104 as possible DA 102 may also prevent the disclosure of sensitive data by performing anonymization on sensitive data that may have otherwise been released.

Data 104 may be stored in a relational database or a non-relational database. DA 102 may receive data 104 from one or more sources and store the received data 104 across records of an input table 106. In an embodiment, input table 106 may include a table in a column-store or in-memory database 105. Organizing data 104 into a column-store, in-memory database 105 may enable DA 102 to perform various anonymization operations (e.g., such as sorting) very quickly relative to other storage mechanisms (such as disk storage in a relational database).

The data of input table 106 may be organized into a number of records, each record including a number of data values. The various records may correspond to one or more individuals or organizations about which data 104 was collected. Each record may include values which correspond to an attribute 108 that identifies what the particular values represent. Example attributes 108 may include name, social security number, salary, medical history, age, address, account balance, credit score, employer, education, relationship status, etc. <John Smith:43:New York> may be an example record with values for the attributes name, age, and location. As shown in the example of FIG. 1, input table 106 may include attributes 108, and DA 102 may receive or process a subset of those attributes 108 in the manner described herein.

In column-oriented database 105, attribute 108 may correspond to a row of input table 106 and may indicate what information is stored in the row, and each column may correspond to a particular record. In a row-oriented or relational database, the row and column designations may be reversed, such that each row corresponds to a record, and each column an attribute 108.

In an embodiment, different attributes 108 may be associated with different levels of privacy 110. Each privacy level 110 may indicate to what level of precision a particular individual can be identified or distinguished from one or more other individuals about whom PII 103 exists within data 104. Privacy 110 may be an indicator of how much or to what degree PII 103 exists within the values of the various attributes 108.

For example, explicit identifier information 110A may indicate that a particular value of an attribute 108 may be used to identify a specific individual or company or record from the data 104. In an embodiment, an explicit identifier 110A value may include a value distinguishable from other values for a particular attribute 108. Example explicit identifiers 110A may include name, social security number, and address.

In an embodiment, privacy 110 designations of particular attributes 108 may be designated relative to the values of other collected data 104. In different data sets 104, the privacy 110 of a particular attribute 108 may vary. For example, in a first data set with only one individual named "Mike Smith," the name attribute may be an explicit identifier 110A. However, in another data set in which data is only collected from individuals named "Mike Smith," the name attribute may not be an explicit identifier 110A, and may not be PII 103 at all.

A quasi-identifier 110B may indicate an attribute 108 or group of attributes 108 whose value when considered together with one or more other attributes 108 (e.g., quasi-identifiers 110B) can potentially identify an individual record from data 104. Example quasi-identifiers 110B may include zip code, birthday, and gender. Any one of these values, when taken alone, may not be enough to distinguish or identify a particular individual or record from input table 106 relative to the other individuals. However, it is possible that (depending on the actual data values of the collected data 104) that any or particular combinations of the quasi attributes 110B may be used to identify an individual in the data set. For example, zip code and birthday may be enough to identify a specific individual in a particular data set. In an embodiment, a quasi-identifier 110B may need to be combined with one or more other quasi-identifiers 110B to identify or distinguish a particular individual or record.

A sensitive identifier 110C may include values (corresponding to an attribute 108) whose significance may be derived through attribution with a specific individual or record. Example sensitive attributes include age, health status, and salary. For example, knowing the identity of a specific an individual about whom particular salary information was collected may be sensitive information 110C. For example, knowing that Rachel Burns is earning $100,000/year may be sensitive information 110C. However, knowing that someone in a study is earning $100,000/year without knowing the identity to be Rachel Burn may not constitute sensitive information 110C. Or for example, in a first data set a value such as "Cancer" may be sensitive 110C to the extent it is attributable to any particular individual in which only a subsection of the data records have "Cancer" values. However in a study of cancer patients, "Cancer" may not be sensitive 110C.

In an embodiment, input table 106 may include the attributes: name, city, birthdate, and salary. DA 102 may receive an indication or designation from a user or administrator who is familiar with values of data 104) as to which attributes 108 correspond to which privacy levels 110. For example, in a first data set, name may be explicit 110A, city and birthdate may be quasi 110B, and salary may be sensitive 110C. However, in a second data set with the same attributes 108 (but different values) the privacy designations 110 may be different.

In addition to being identified with a particular privacy level 110, attributes 108 may also be identified with a particular data type 112. Data type 112 may be an indication of what type of data values are stored in input table 106. Each attribute 108 may include its own data type 112. Three example data types 112 include numeric 112A, hierarchical 112B, and textual 112C. Numeric 112A may indicate that the values of attribute 108 are number values (integer, real, whole, decimal, currency, etc.). An example numeric data value may be salary.

In an embodiment, data type 112 may be applied to quasi attributes 110B as used by DA 102 to perform data anonymization functions. For example, data type 112 for quasi 110B may indicate how to partition the data during the data anonymization process. In an embodiment, different attributes 108 with number values (integer, real, whole, decimal, currency, etc.) may be defined as numerical 112A.

Hierarchical 112B may indicate that the data values adhere to a type of hierarchy, flow, or nesting. Example hierarchical data may include relative positions within a company organizational chart. For example, a company organizational chart may include the Chief Executive Officer (CEO) at the top with different positions flowing out from the root node of CEO that indicate a level of managerial hierarchy within the organization.

Textual 112C may indicate that the attribute 108 includes values that are to be interpreted as alpha-numeric strings or characters. In an embodiment, the textual 112C designation may be used on an attribute 108 that includes only numeric characters and is to be interpreted as textual 112C data rather than number 112A. An example of such data may be a string of numbers that correspond to a personal identifier or social security number. Other example textual data 112C may include name or address information. In an embodiment, address information may be broken down into both a numerical attribute 112A indicating building number, and a textual attribute 112C indicating the name of the road on which the building is located.

To perform data anonymization on the values of input table 106, DA 102 may receive an indication of a DA type 114 and a threshold value 116 from a user or data administrator corresponding to the different attributes 108. DA type 114 may indicate which particular data anonymization technique(s) is to be applied to the values of data 104. In an embodiment, DA 102 may apply any combination of data anonymization techniques such as K-anonymity, diversity, and/or T-closeness, to name just some examples. Threshold value 116 may correspond to the selected or indicate the DA type 114, and indicate a level or degree of anonymization.

In some embodiments, in K-anonymity, the property K (i.e., threshold 116) may indicate that each record in anonymized data 120 must be indistinguishable from at least K−1 other records. Anonymized data 120 may include the published or output data after data anonymization, in which PIT 103 has been reduced, grouped, removed, or otherwise obscured.

In an embodiment, DA 102 may apply K-anonymity with respect to the quasi-identifiers 110B. As is discussed in greater detail below, DA 102 may group records into various equivalence classes 118 based on a similarity or overlap of their quasi-identifier 110B values. Each equivalence class 118 may include at least K records (threshold 116) grouped based on various ranges for values as determined by DA 102.

In some embodiments, in L-diversity, the distribution of values for sensitive identifiers 110C within an equivalence class 118 must be at least L (i.e., threshold 116). For example, if salary is a sensitive identifier 110C, and L is 5, then in an equivalence class 118 for the anonymized or output data set 120, there must be at least 5 unique salary values in an equivalence class. In an embodiment, if there are fewer than the specified threshold 116 of records in an equivalence class 118, DA 102 may either suppress the records or combine the records with another equivalence class 118 to satisfy the threshold 116.

In some embodiments, T-closeness is a further refinement of L-diversity, in which the distribution of values for the sensitive identifier 110C within an equivalence class 118 is within T of the distribution of the sensitive identifier 110C for the entire data set.

Solely for purposes of illustration, and not limitation, the operations of DA 102 are described with respect to K-anonymity 114, unless otherwise specified. In an embodiment, there may be two primary steps to performing the selected DA type 114 (e.g., K-anonymity) on the values of data 104 from input table 106. The first step may be determining or selecting which attribute(s) 108 to anonymize. The second step may be actually performing the data anonymization functionality on the actual values of the selected attribute(s) 108.

In an embodiment, DA 102 may also perform L-diversity in addition to or in lieu of K-anonymity. For example, based on the output equivalence classes 118 of K-anonymity, DA 102 may check the sensitive 110C data values to determine whether the L value (threshold 116) is also satisfied. If the L threshold 116 is satisfied, the anonymized data 120 may be output to table 126 without further processing. However, if L threshold 116 is not satisfied, DA 102 may then anonymize any quasi data values 110B prior to outputting the resultant data set 120.

In an embodiment, DA 102 may verify both K-anonymity and L-diversity are satisfied for data 104 prior to output to table 126. DA 102 may split a partition based on quasi attributes 110B, and DA 102 may check to see whether both K threshold 116 and L threshold 116 values are satisfied for each sub-partition (which may be performed in parallel). In an embodiment, DA 102 may check both L and K thresholds 116 at the same time.

During partitioning, DA 102 may check to verify whether the various sub-partitions satisfy the indicated K and L thresholds 116. In an embodiment, DA 102 may identify any sub-partitions that cannot satisfy either the K or L thresholds 116 and set a disallow split flag to avoid a further split on this partition. This may save partitioning resources from attempting further splits or partitionings on data sets that will not satisfy one or both thresholds 116. Example pseudo code related to this is provide below:

```
anonymize(partition){
    If (not exists allowable cut on partition) {
        store the partition to final equvilance class list.
        return;
    }
    dim = chooseDimension(partion);
    sub_partitons = split(partition, dim);
    for each partition in sub partitions{
        anonymize(partition);
    }
}
```

In an embodiment, the partition may be added to the list of equivalence classes 118. In an embodiment, if any values or partitions remain that do not or cannot satisfy K and/or L thresholds 116, the remaining values may be suppressed from being provided as part of anonymized data 120 (and a user may be notified).

DA 102 may use the privacy 110 and data type 112 information to perform data anonymization on PII 103 using K-anonymity. For example, DA 102 may anonymize values corresponding to the indicated quasi-identifiers 110B to generate one or more equivalence classes 118 which are then output to output table 126. Output table 126 is used to store anonymized data 120.

In an embodiment, DA 102 may suppress explicit identifiers 110A and prevent their release into output table 126. In an embodiment, in K-anonymity, DA 102 may not anonymize sensitive identifiers 110O, but instead anonymize the quasi-identifiers 110B to prevent any association between the sensitive information 110C and the identity of an individual using PII 103. However, DA 102 may apply L-diversity to anonymize the values of sensitive identifiers 110C.

DA 102 may generate one or more equivalence classes 118 as part of the data anonymization process. An equivalence class 118 may include a set of records within an anonymized data set 120 that have the same, similar, or overlapping values (or values that fall within a range) for one or more quasi identifiers 110B. For example, a group of records that share the same zip code, city, birthdate, and/or first name may belong to the same equivalence class 118. Other examples include identifiers that share one or more characters, or ages that fall within a range.

In an embodiment, DA 102 may calculate and use a width 122 of the various quasi-attributes 110B to determine or select which atttibute(s) 108 to anonymize. Width 122 may be an indicator of how wide a range of values exist in data 104 for a particular attribute 108. In the case of K-anonymity, DA 102 may determine the width 122 for the various quasi-identifiers 110B and/or various combinations thereof.

In an embodiment, DA 102 may determine the relative widths 122 of the attributes 108 from the group of identified quasi-identifiers 110B for satisfying the K-anonymity and/or L-diversity thresholds 116. When data 104 is anonymized or abstracted, there may be a degree of information loss that occurs as part of the data anonymization process. In order to reduce the amount of information loss, DA 102 may select the attribute(s) 108 with the greatest width 122 or range of values for data anonymization. Selecting the attribute 108 with the greatest width 122 may reduce the amount of information loss that occurs during data anonymization. However, to accurately perform a width analysis across different attributes 108, DA 102 may need to account for the various different data types 112 corresponding to those attributes 108.

Normalized certainty penalty (NCP) measures information loss (e.g., width 122) or potential information loss for a single generated equivalence class 118 (partition) of data 104 pertaining to anonymizing a selected quasi-attribute 110B. In an embodiment, DA 102 may include different NCP calculation techniques based on the different data types 112 corresponding to the various attributes 108. DA 102 may calculate NCP for the various attributes 108 to determine which has the greatest width 122 or NCP. In an embodiment, the attribute 108 with the greatest width 122 or least information loss may be selected for anonymization by DA 102 (if threshold 116 is also satisfied by the anonymization of the selected attribute 108).

In an embodiment, NCP may be calculated and used to recursively split a data set into different partitions. For example, during a first iteration, an attribute 108 with a greatest NCP may be selected to be split. For example, if there are two quasi attributes age and workclass that have NCPs of 0.5 and 0.25, respectively, age may be selected to partition the data set during a first iteration. After the first iteration, the NCPs may be recalculated for the various quasi attributes, and if the threshold 116 has not been met, then the quasi attribute with the remaining highest NCP (which may be the same or different attribute) may be selected upon which to partition the data set during the second iteration. This process may be performed recursively until threshold 116 is satisfied.

In some embodiments, for numerical attributes 112A, the NCP (width 122) of an equivalence class 118 (partition P) on an attribute 108 may be defined as:

$$NCP_{A_{Num}}(P) = \frac{\max^P_{A_{num}} - \min^P_{A_{num}}}{\max_{A_{Num}} - \min_{A_{Num}}}$$

The numerator and denominator represent the ranges of the attribute $A_{num}$ for the partition P and the entire attribute domain, respectively. As used herein, in some embodiments, partition P and equivalence class 118 may be used interchangeably, wherein both may refer to a grouping of values from input table 106. For example, a partition may have an interval or actual data values ranging from 20 to 30 on attribute "Age." The partition may also include an interval or range of possible data values ranging from 20 to 60 in the entire attribute domain (of data 104). Then, for example, the NCP for the Age attribute may be calculated as (30-20)/(60-20)=0.25.

In some embodiments, for a hierarchical data type 112B, NCP (width 122) may be calculated as:

$$NCP_{A_{Cat}}(P) = \frac{card(u)}{A_{Cat}}$$

Figure 4:
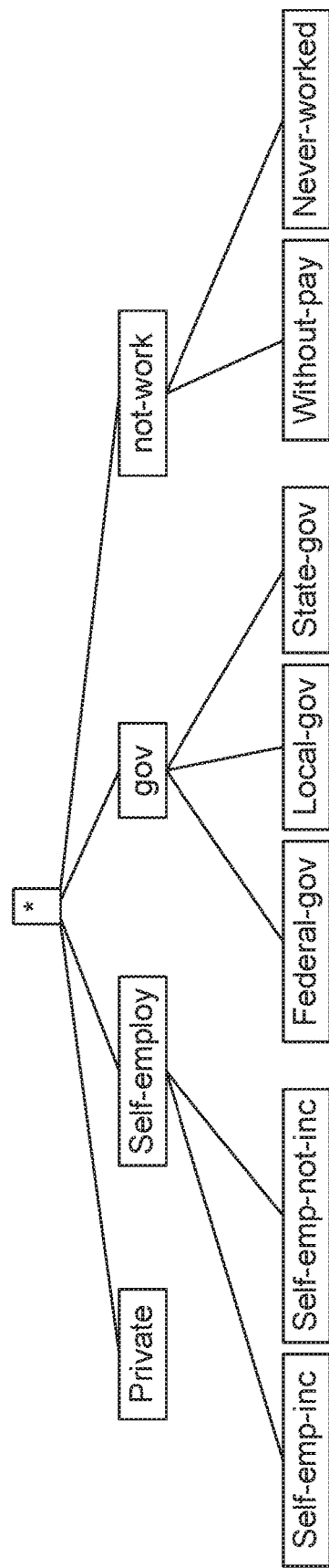
FIG. 4 is a block diagram illustrating example data anonymization functionality with respect to a hierarchical data type, according to an embodiment.

"u" may be the lowest common ancestor for $A_{Cat}$ values included in P. "Card(u)" may be the number of leaves (i.e., attribute values) in the sub-tree of u, which may be the root node of the example partition shown in FIG. 4. FIG. 4 is a block diagram 400 illustrating example data anonymization functionality with respect to a hierarchical data type, according to an embodiment.

For example, in the hierarchy of attribute "Workclass" shown in FIG. 4, the root node * contains 8 leaves. If a partition's root is "self-employ," it contains 2 leaves. Thus, the normalized width (NCP) for the partition would be (2/8)=0.25.

In some embodiments, for a textual data type 112C, the NCP (width 122) be calculated as:

$$NCP_{A_{Txt}}(P) = \frac{n_p \cdot \sum_{i=1}^{n_p} \text{Anonymized}(t_i)}{A_{txt} \cdot n_A}$$

The numerator and denominator represent the total number of anonymized characters of attribute $A_{Txt}$ for the partition P, and the total number of characters of attribute $A_{num}$ for data 104, respectively. $n_p$ is the number of records in the partition, and $n_a$ is the number of records of the entire dataset 104. Anonymized($t_i$) is the number of anonymized characters for tuple $t_i$. $A_{txt}$ is the total number of characters of attribute $A_{Txt}$ for data 104.

Figure 5:
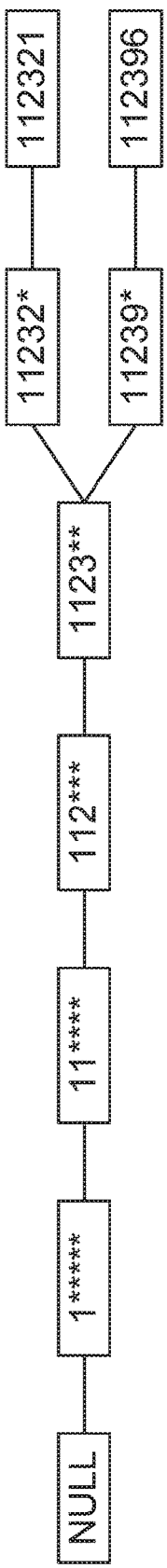
FIG. 5 is a block diagram illustrating example data anonymization functionality with respect to a textual data type, according to an embodiment.

A partition may contain two records with values "112321" and "112396" on attribute "Final_Weight" which is identified as textual 112C. While there may be no specified hierarchy or nesting for Final_Weight, DA 102 may create an example internal hierarchy as shown in FIG. 5. FIG. 5 is a block diagram 500 illustrating example data anonymization functionality with respect to a textual data type, according to an embodiment.

The hierarchy may be generated based on identification of a common string or root (if any). As shown in FIG. 5, the two values may be generalized to a common string, also known as a root, "1123". The number of anonymized characters for the root is 2 (as indicated by the ). The number of characters anonymized in the partition is 4. The total number of characters for the data set is 12 (6 in each value, though in other examples, the number of characters of different values may vary), and there are 2 records in the partition, and 8 total records in the database. The NCP may then be calculated as: 2*4/12*8=0.08.

In an embodiment, the width 122 may also be weighted. Weight 124 may indicate an importance or relative importance of the quasi identifiers 110B. The greater the weight, the more important the values of the attribute 108 may be to the research study or data integrity. In some embodiments, weighted NCP may be calculated as follows:

$$WNCP_{A^i}(P) = W_i * NCP_{A_i}(P)$$

In an embodiment, privacy 110, data type 112, and weight 124 may be provided to DA 102 in the form of extensible markup language (XML). In an example embodiment, in which the Age attribute has a weight of 100, the XML may indicate <quasiAttribute name="Age" type="number" weight=100/>.

As noted above, the attribute 108 (quasi-attribute 110B) with the highest weighted NCP may then be selected for partitioning (e.g., data anonymization). As used herein, in some embodiments, partitioning and data anonymization may be used interchangeably to refer to the processing performed by DA 102 that removes or obscures PII 103 from data 104, and is used to generate anonymized data 120.

In an embodiment, DA 102 may recursively perform partitioning or partition splitting based on data type 112, until the threshold 116 for the selected DA type 114 is satisfied. For example, DA 102 may recursively partition data 104 based on an attribute 108 with the greatest width 122 until each of the generated equivalence classes 118 includes at least K records (satisfying threshold 116) for K-anonymity (DA type 114).

In performing data anonymization or partitioning for numerical attributes 112A, a partition or data set of input table 106 may be split into two partitions (or data sets) based on the median value of an attribute 108. An example, numerical partitioning split algorithm is shown below.

```
splitNumerical(partition, dimension){
    median = find the median value on dimension for partition P;
    for each tuple t_i in partition on dimension {
        if (t_i < median)
            store t_i to p_smaller;
        else
            store t_i to p_bigger;
```

```
      if (|p_smaller| >= k and {p_bigger|>= k) {
         return p_smaller ∪ p_bigger;
      }
      else {
         set split allowable to false for partition P on dimension;
         return P;
      }
   }
}
```

For hierarchical attributes 112B, DA 102 may create a hierarchical tree on the attribute 108 with one root and a number of sub-groups. DA 102 may ensure that each sub-group includes at least K records. If a particular sub-group does not include at least K records, then it is moved into an "Others" sub-group (which may not be one of the original sub-groups from input table 106).

As part of the partitioning process (for numerical data types 112A), any larger sub-groups that include more than 2K−1 records may be split into two sub-groups. At the end of the partitioning process, each remaining sub-group or equivalence class 118 may include at least K and no more than 2K−1 records. In an embodiment, any sub-groups with fewer than K records may either be suppressed (e.g., excluded from anonymized data 120) or combined with other equivalence classes 118.

For hierarchical data 112B or textual data 112C, the number of sub groups may be determined by the number of children for the current parent. In an embodiment, a partition with greater than K records could be partitioned into further sub-groups. Or, for example, any sub-groups or equivalence classes with fewer than K records may be combined into another group.

An example, hierarchical partition split algorithm is shown below.

```
splitHierarchical (partition, dimension){
   root = get partition root node on dimension;
   for each child r_i of root{
      for each tuple t_j of partition on dimension{
         if (r_i covers t_j) {
            stores t_j into p_i;
            remove t_j from partition;
         }
      }
      replace root with r_i for the p_i sub partition
   }
   store the rest of tuples into p_other;
   set root to the partition root;
   set split allowable to false fix sub partition p_other on dimension;
   merge p_i, which has tuples less then k, into p_others;
   return p_i ∪ p_ohters
}
```

In some embodiments, splitting or partitioning textual attributes 112C begins with identifying a common string (if any) for the tuples or records. The tuples are then grouped into sub-groups with a common string (root). For example, starting with an empty string, DA 102 may scan values to identify a common character amongst multiple values of the attribute 108. If a common character is identified, it is added to the common string (root) in each iteration. At the end, the partition or data set is split into sub-partitions or equivalence classes 118, each sub-partition having the same root. In an embodiment, in partitioning of textual values 112C, DA 102 may generate a text-based hierarchy. An example textual partitioning algorithm is shown below.

```
splitTextual(partition, dimension){
   root = get partition root node on dimension;
   count = root.size( ) + 1;
   while (partition.size( ) > 0) {
      newroot = substring(t_0, count);
      for each tuple t_i in partition on dimension {
         r_i = substring(t_i, count);
         if (newroot == r_i){
            store t_i to p_i;
            remove t_i from partition;
         }
      }
      replace root with newroot for partition p_i;
   }
   merge p_i, which has tuples less then k, into p_others;
   set root to the partition root;
   set split allowable to false for sub partition p_other on dimension;
   return p_i ∪ p_ohters;
}
```

Table 1 below is an example of data that may be stored in input table 106 and received or made available to DA 102. The example data includes 8 records and 5 attributes 108. The attributes 108 may include the following privacy 110 designations: ID-explicit and Salary-sensitive, and Age, WorkClass, and Final_Weight may be quasi attributes 110B.

In some embodiments, the selected DA type 114 may be K-anonymity, and the threshold K 116 may be 2. The quasi-attributes 110B may include the following data type 112 designations: Age-numerical, Work:Class-hierarchical, and Final Weight-textual attribute 112C.

TABLE 1

(Input Table 106)

| ID | Age | WorkClass | Final_Weight | Salary |
|----|-----|-----------|--------------|--------|
| 1 | 39 | State-gov | 112316 | <=50k |
| 2 | 50 | Self-employ | 215682 | <=50k |
| 3 | 38 | Private | 215646 | <=50k |
| 4 | 52 | Self-employ | 215642 | >50k |
| 5 | 31 | Private | 215681 | >50k |
| 6 | 30 | State-gov | 112319 | >50k |
| 7 | 25 | Self-employ | 112396 | <=50k |
| 8 | 56 | Local-gov | 112321 | >50k |

An example anonymization of the values of Table 1 based on Age, with K=2, is shown below in Table 2. As may be seen in Table 2, there are 4 equivalence classes 118 of Age, each containing at least (K) 2 records. Tables 2-5 below illustrate example output tables 126 which may be produced as a result of data anonymization by DA 102.

TABLE 2

(Anonymized based on Age, K = 2), GCP = 21.77%

| ID | Age | WorkClass | Final_Weight | Salary |
|----|-----|-----------|--------------|--------|
| 6 | 25-30 | State-gov | 112319 | >50k |
| 7 | 25-30 | Self-employ | 112396 | <=50k |
| 3 | 31-38 | Private | 215646 | <=50k |
| 5 | 31-38 | Private | 215681 | >50k |
| 1 | 39-50 | State-gov | 112316 | <=50k |
| 2 | 39-50 | Self-employ | 215682 | <=50k |
| 4 | 52-56 | Self-employ | 215642 | >50k |
| 8 | 52-56 | Local-gov | 112321 | >50 |

The values of Table 1 K-anonymized based on Workclass, with K=2, generates 3 equivalence classes as follows in Table 3.

TABLE 3

(Anonymized based on WorkClass, K = 2), GCP = 14.06%

| ID | Age | WorkClass | Final_Weight | Salary |
|---|---|---|---|---|
| 3 | 38 | Private | 215646 | <=50k |
| 5 | 31 | Private | 215681 | >50k |
| 2 | 50 | Self-employ | 215682 | <=50k |
| 4 | 52 | Self-employ | 215642 | >50k |
| 7 | 25 | Self-employ | 112396 | <=50k |
| 1 | 39 | Gov | 112316 | >50k |
| 6 | 30 | Gov | 112319 | >50k |
| 8 | 56 | Gov | 112321 | >50k |

The values of Table 1 K-anonymized based on Final Weight, with K=2, generates 4 equivalence classes as shown in Table 4 below.

TABLE 4

(Anonymized based on Final_Weight, K = 2), GCP = 2.6%

| ID | Age | WorkClass | Final_Weight | Salary |
|---|---|---|---|---|
| 7 | 25 | Self-employ | 1123** | <=50k |
| 8 | 56 | Local-gov | 1123** | >50k |
| 1 | 39 | State-gov | 11231* | <=50k |
| 6 | 30 | State-gov | 11231* | >50k |
| 3 | 38 | Private | 21564* | <=50k |
| 4 | 52 | Self-employ | 21564* | >50k |
| 2 | 50 | Self-employ | 21568* | <=50k |
| 5 | 31 | Private | 21568* | >50k |

An example of the values of Table 1 K-anonymized based on a combination of quasi-attributes 110A is shown below in Table 5. In the example of Table 5, the quasi-attributes 110B Age, WorkClass, and Final_Weight are used to generate 4 equivalence classes 118. In another embodiment, DA 102 may generate or process different combinations of quasi-attributes 110B as well, such as Age and WorkClass, Age and Final Weight, and/or WorkClass and Final_Weight.

TABLE 5

(Anonymized based on Age, WorkClass, and Final_Weight, K = 2), GCP = 21.18%

| ID | Age | WorkClass | Final_Weight | Salary |
|---|---|---|---|---|
| 1 | 39-56 | Gov | 1123** | <=50k |
| 8 | 39-56 | Gov | 1123** | >50k |
| 6 | 25-30 | * | 1123** | >50k |
| 7 | 25-30 | * | 1123** | <=50k |
| 3 | 31-38 | Private | 2156** | <=50k |
| 5 | 31-38 | Private | 2156** | >50k |
| 2 | 50-52 | Self-employ | 2156** | <=50k |
| 4 | 50-52 | Self-employ | 2156** | >50k |

As shown in the examples above, a global certainty penalty (GCP) may be calculated for each example partitioning of data 104 based on various (combinations of) quasi-attributes 110B. In some embodiments, GCP for a table (T) may be calculated as follows:

$$GCP(T) = \frac{\sum_{i=1}^{m} G_i \cdot NCP(P_i)}{d \cdot n}$$

"n" may denote the number of records in the original table, "d" may indicate the number of quasi-identifiers 110B. "m" may be the number of equivalence classes. $G_i$ is the number of records in the equivalence class $P_i$. GCP may produce a result between 0 and 1, or 0% and 100% if represented as a percentage.

As may be seen from the example just described, the quasi-attribute 110B with the least information loss may be the textual attribute 112C, Final_Weight. For example, in anonymizing the data 104 of Table 1 based on K-anonymity with K=2, DA 102 may use the quasi-identifier Final_Weight and produce the anonymized data 120 in the output table 126 of Table 4 shown above. In an embodiment, a quasi-attribute 110B may not be a single attribute (e.g., row), but may actually be several user-indicated attributes which together form a quasi-attribute 110B. As such, DA 102 may perform data anonymization on several attributes 108 which comprise a quasi-attribute 110B, simultaneously, together, or in parallel. The examples of Tables 2-4 showing a singular attribute 108 as a quasi-attribute 110B are exemplary only.

As described herein, DA 102 may perform data anonymization across a plurality of nodes and in parallel. For example, the values of input table 106 may be initially partitioned or separated based on the various quasi-attributes 108 or data type 112. The partitions may then be distributed to different nodes for parallel processing, and may be performed with regards to each attribute 108 to perform the above-referenced calculations in determining how to anonymize the values of input table 016 with the least amount of information loss.

As noted above, in addition or alternative to performing K-anonymity, DA 102 may receive an indication (DA type 114) to perform L-diversity anonymization. K-anonymity may be used by DA 102 to avoid, prevent, or otherwise minimize the disclosure of identifying information about the subjects of data 104. L-diversity may be used by DA 102 to prevent the disclosure sensitive information, or prevent the attribution of particular sensitive data with groups of individuals. While K-anonymization is performed based on quasi-attributes 110B, it is not performed with respect to sensitive information 110C.

DA 102 may be configured to perform L-diversity anonymization on one or more quasi attributes 110B until one or more sensitive attributes 110C satisfy L threshold 116. DA 102 may check L-diversity threshold 116 in addition to or alternative to K-anonymization threshold 116 based on a user indication in DA type 114. In an embodiment, L-diversity may require each group of data (partition or equivalence class 118) to include at least L unique values (associated with sensitive identifiers 110C). In an embodiment, any group that has fewer than L values may be combined with another group or suppressed from being provided in output table 126. As described herein, partitioning based on L-diversity may include combining partitions to satisfy L threshold 116.

Table 6 shows an example K-anonymity data anonymization based on the quasi-attributes Age and Zipcode.

TABLE 6

K anonymization example

| Age | Zipcode | Disease |
|---|---|---|
| [25-26] | [53710-53711] | Flu |
| [25-26] | [53710-53711] | Flu |
| [25-28] | 53712 | Hepatitis |
| [25-28] | 53712 | Hepatitis |
| [27-28] | [53710-53711] | Broken Arm |
| [27-28] | [53710-53711] | Broken Arm |

As may be seen from the example data of Table 6, 3 equivalence classes are produced. However, the different equivalence classes may include the same values for the sensitive data—Disease. For example, both records of the first equivalence class have the value Flu. As such, the equivalence classes may fail an L-diversity requirement of each equivalence class having at least two different sensitive attributes.

Having overlapping or not enough unique values with regard to sensitive data 110C may put user confidentiality at risk by exposing the sensitive information that could be attributed to a group of one or more users. For example, consider the illustrative case where everyone in the study ages 25-26 who lives at 53712 zip code is known to have hepatitis. As such, DA 102 may perform L-diversity anonymization to avoid such potential disclosures of attributable sensitive information. Table 7 shows an example of L-diversity data anonymization based on an L threshold 116 value of 2 for the data shown in Table 6.

TABLE 7

L-diversity example

| Age | Zipcode | Disease |
|---|---|---|
| [25-26] | [53710-53711] | Flu |
| [25-26] | [53710-53711] | Hepatitis |
| [25-28] | 53712 | Flu |
| [25-28] | 53712 | Hepatitis |
| [27-28] | [53710-53711] | Flu |
| [27-28] | [53710-53711] | Broken Arm |

DA 102 enables a user to select K-anonymity, L-diversity, or both, for numerical, hierarchical, and/or textual data types 112. As noted above, while K-anonymity anonymizes based on one or more quasi-attributes 110B, L-diversity may anonymize based on one or more quasi-attributes 110B to ensure the diversity of sensitive attributes 110C. For example, in L-diversity, while partitioning may be performed based on quasi-attributes 110B (in a similar manner described with respect to K-anonymity), one or more sensitive attributes 110C may be checked to determine if they satisfy L threshold 116. In different embodiments, the partitioning performed to satisfy the K and L thresholds 116, may use the same or different quasi attributes 110B. Both anonymization processes may be performed recursively until the respective or thresholds 116 (K value and L value) are satisfied.

NCP values (e.g., width 122) as referenced above may be used with respect to performing partition splitting for both K-anonymity and/or L-diversity. The calculation of NCP values may be performed similarly as described above for both data anonymization techniques across the various data types 112.

In performing K-anonymity, DA 102 may recursively check after each partition split whether K 116 has been satisfied. If K 116 cannot be satisfied, the partitioning or split process may stop and K-anonymity may be complete. The same applies to DA 102 performing L-diversity anonymization (e.g., data anonymization on quasi-attributes 110B to satisfy L threshold 116, which may include combining or splitting partitions). After each L-diversity partition, DA 102 may check to see if L 116 has been satisfied, and may continue L-diversity anonymization until a partition cannot be further split and L 116 is satisfied for each partition (e.g., sub-partition). If DA 102 is performing both K-anonymity and L-data anonymizations, then DA 102 may ensure both K 116 and L 116 are satisfied for each equivalence class 118 (and that no further partitioning can be performed) prior to outputting anonymized data 120 to output table 126.

Example pseudo code is shown below that illustrates an embodiment of performing L and K checks.

```
splitTextual(partition, dimension){
    root = get partition root node on dimension;
    count = root.size( ) + 1;
    while (partition.size( ) > 0) {
        newroot = substring(t_0, count);
        for each tuple t_i in partition on dimension {
            r_i = substring(t_i, count);
            if(newroot == r_i){
                store t_i to p_i;
                remove t_i from partition;
            }
        }
        // check if sub partition p_i satisfies requirement.
        If (checkModelCondition(p_i) == true) {
            set newroot as the root for partition p_i;
        }
        else {
            // merge p_i into p_others
            p_others = p_i ∪ p_others;
            set root as the partition root for partition p_other;
            set split allowable for false for sub partition p_other on dimension;
        }
    }
    store the rest of tuples into p_other;
    // if combined partition doesn't satisfy, split failed and return
    partition passed in
    If(checkModelCondition(p_other) == false) {
        set split allowable to false for partition P on dimension;
        return P;
    }
    else {
        // return sub partitions
        return p_i ∪ p_ohters;
    }
}
```

While ensuring that an equivalence class 118 satisfies both K-anonymity and L-diversity thresholds 116 enables a user to further protect data, using anonymization techniques to satisfy both thresholds 116 may also increase the amount of information loss for the final or output dataset. A user wanting to anonymize data 104 may balance anonymization and privacy 110 considerations with information loss in determining DA type 114.

In an embodiment, user may provide a secondary threshold 116 value that indicates a maximum acceptable information loss value for K-anonymity, L-diversity, or a combination of both. If, the secondary threshold 116 cannot be satisfied then an error or notification may be returned to the user indicating it is not possible.

Table 8 shows example input data to be anonymized. In the example below, Age, WorkClass, and Final_Weight may be quasi-attributes 110B and Occupation may be a sensitive attribute 110C.

TABLE 8

Data Input for Anonymization

| ID | Age | WorkClass | Final_Weight | Occupation |
|---|---|---|---|---|
| 1 | 39 | State-gov | 112316 | Adm-clerical |
| 2 | 50 | Self-emp-not-inc | 215682 | Farming-fishing |
| 3 | 38 | Private | 215646 | Handlers-cleaners |
| 4 | 52 | Self-emp-not-inc | 215642 | Exec-managerial |

TABLE 8-continued

Data Input for Anonymization

| ID | Age | WorkClass | Final_Weight | Occupation |
|----|-----|-----------|--------------|------------|
| 5 | 31 | Private | 215681 | Prof-specialty |
| 6 | 30 | State-gov | 112319 | Prof-specialty |
| 7 | 25 | Self-emp-not-inc | 112396 | Prof-specialty |
| 8 | 56 | Local-gov | 112321 | Tech-support |

Table 9 shows an example of how the input data of Table 8 may be anonymized using K-anonymity with a K value of 2. In the example shown, K may be applied to all of the quasi-attributes to generate 4 equivalence classes. Additionally, the GCP (information loss) may be calculated by DA 102 to be 30.90%.

TABLE 9

K-anonymization, K = 2

| ID | Age | WorkClass | Final_Weight | Occupation |
|----|-----|-----------|--------------|------------|
| 6 | 25-30 | * | 1123** | Prof-specialty |
| 7 | 25-30 | * | 1123** | Prof-specialty |
| 3 | 31-38 | Private | 2156** | Handlers-cleaners |
| 5 | 31-38 | Private | 2156** | Prof-specialty |
| 1 | 39-56 | gov | 1123** | Adm-clerical |
| 8 | 39-56 | gov | 1123** | Tech-support |
| 2 | 50-52 | Self-emp-not-inc | 2156** | Farming-fishing |
| 4 | 50-52 | Self-emp-not-inc | 2156** | Exec-managerial |

GCP = 30.90%

Table 10 shows an example of how the input data of Table 8 may be anonymized to satisfy L-diversity with an L, value of 2. The result may generate 3 equivalence classes. The GCP (information loss) may be computed to be 47.38%.

TABLE 10

L-diversity, L = 2

| ID | Age | WorkClass | Final_Weight | Occupation |
|----|-----|-----------|--------------|------------|
| 2 | 25-52 | Self-emp-not-inc | ****** | Farming-fishing |
| 4 | 25-52 | Self-emp-not-inc | ****** | Exec-managerial |
| 7 | 25-52 | Self-emp-not-inc | ****** | Prof-specialty |
| 1 | 30-56 | gov | 1123** | Adm-clerical |
| 6 | 30-56 | gov | 1123** | Prof-specialty |
| 8 | 30-56 | gov | 1123** | Tech-support |
| 3 | 31-38 | Private | 2156** | Handlers-cleaners |
| 5 | 31-38 | Private | 2156** | Prof-specialty |

GCP = 47.38%

Table 11 shows an example of output table 126 if both K-anonymity and L-diversity are requested by a user to be satisfied by data output from the input data of Table 8, with both K and L=2.

TABLE 11

K-anonymity & L-diversity

| ID | Age | WorkClass | Final_Weight | Occupation |
|----|-----|-----------|--------------|------------|
| 2 | 25-52 | Self-emp-not-inc | ****** | Farming-fishing |
| 4 | 25-52 | Self-emp-not-inc | ****** | Exec-managerial |
| 7 | 25-52 | Self-emp-not-inc | ****** | Prof-specialty |
| 1 | 30-56 | gov | 1123** | Adm-clerical |
| 6 | 30-56 | gov | 1123** | Prof-specialty |
| 8 | 30-56 | gov | 1123** | Tech-support |
| 3 | 31-38 | Private | 2156** | Handlers-cleaners |
| 5 | 31-38 | Private | 2156** | Prof-specialty |

As described above, DA 102 may perform data anonymization from the top-down. In the top-down approach to data anonymization, DA 102 may begin by treating the data from input table 106 as an equivalence class. Then, DA 102 may initially and recursively partition the initial equivalence class 118 into smaller equivalence classes 118 until smaller equivalence classes cannot be further partitioned and the K and/or L thresholds 116 are satisfied for each final equivalence class. DA 102 may then output the anonymized data 120. In an embodiment, partitioning may include combining two or more partitions to satisfy an indicated threshold 116.

However, as described above, one of the concerns with data anonymization is information loss (as measured by NCP and GCP values). Through the data anonymization process, data may be grouped, abstracted, or suppressed in order to ensure the anonymization threshold 116 is satisfied and the individual and/or sensitive data is protected. However, this grouping, abstraction and/or suppression of data may cause the loss of the some of the original data in the resultant anonymized data 120.

One way to minimize information loss is to use a bottom-up approach to data anonymization. In an embodiment, DA 102 may perform data anonymization from the bottom-up or from the top-down. One of the advantages of the bottom-up approach is that it minimizes the information loss that occurs through the data anonymization process. However, the downside is that the bottom-up approach often requires additional processing resources and/or time relative the top-down approach for the same data set. In an embodiment, a user may indicate or choose which approach(es) to use as DA type 114.

In a traditional bottom-up approach, each tuple or record may be treated as an individual group or equivalence class and then be merged with other groups. Then, after merging, larger groups (with more than 2K tuples) are then divided again into smaller groups. This combination and splitting may consume greater resources than a top-down approach and may be performed until the K threshold is satisfied.

In an embodiment, DA 102 may perform a modified bottom-up approach that enables DA 102 to consume fewer processing resources and/or time compared to traditional bottom-up processing. An exemplary bottom-up processing as performed by DA 102 is described in reference to FIG. 2.

Figure 2:
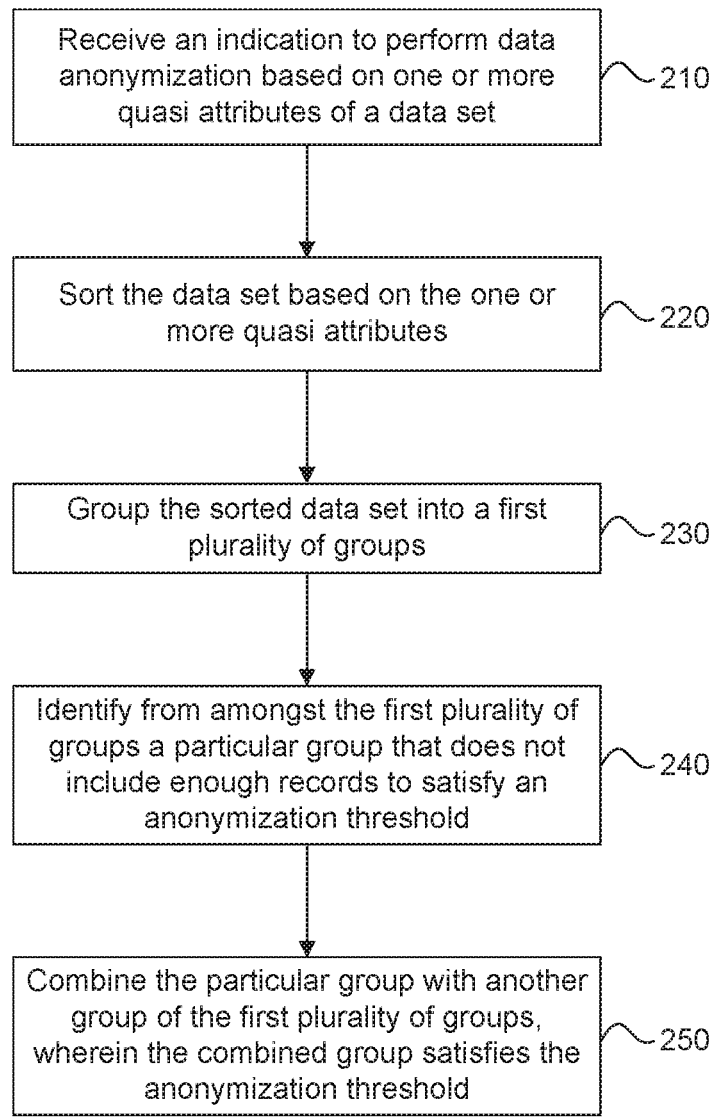
FIG. 2 is a flowchart illustrating a process for data anonymization, according to some embodiments.

FIG. 2 is a flowchart illustrating a process 200 for data anonymization, according to some embodiments. Method 200 can be performed by processing logic that can comprise hardware (e.g., circuitry, dedicated logic, programmable logic, microcode, etc.), software (e.g., instructions executing on a processing device or a combination thereof. It is to be appreciated that not all steps may be needed to perform the disclosure provided herein. Further, some of the steps may be performed simultaneously, or in a different order than shown in FIG. 2, as will be understood by a person of ordinary skill in the art. Method 200 shall be described with reference to FIG. 1. However, method 200 is not limited to that example embodiment.

In 210, an indication to perform data anonymization based on one or more quasi attributes of a data set is received. For example, in FIG. 1, DA 102 may receive DA type 114 that may indicate whether to perform K-anonymization and/or L-diversity data anonymization on data 104 of input table 106. DA type 114 may further indicate whether a top-down or bottom-up approach is to be performed with respect to the indicated data anonymization algorithms.

In 220, the data set is sorted based on the one or more quasi attributes. For example, DA 102 may sort the various records or tuples of input table 106 based on one or more selected quasi attributes 110B to be used for anonymization (to satisfy K and/or L thresholds 116). Each tuple or record may include values that correspond to the selected quasi attributes 110B.

In 230, the sorted data set is grouped into a first plurality of groups. For example, DA 102 may group the sorted records based on which of the records share value(s) corresponding to the selected quasi identifier(s) 110B. In an embodiment, DA 102 may create groups based on overlapping ranges of values.

In 240, a particular group that does not include enough records to satisfy an anonymization threshold is identified from amongst the first plurality of groups. For example, DA 102 may determine which equivalence class 118 or group of data from input table 106 does not satisfy K threshold 116 and/or L threshold 116 based on which DA type 114 was selected.

In 250, the particular group is combined with another group of the first plurality of groups. For example, DA 102 may combine two or more equivalence classes 118 in order to generate a plurality of equivalence classes 118 that satisfy threshold 116. In an embodiment, DA 102 may combine two groups that do not satisfy threshold 116 to create a combined group. If the combined group does not satisfy threshold 116, the process of FIG. 2 may be recursively performed (in part) and the combined group may be combined with one or more additional groups until the resultant set of groups satisfy the indication threshold 116. The resultant anonymized data 120 may then be output to table 126. In an embodiment, DA 102 may combine of two or more sub groups into a final equivalence class 118 based on determining which combination(s) would result in a smallest NCP.

In an embodiment, the selection as to which groups to combine may be based on NCP value. For example, two groups which do not satisfy threshold(s) 116 with the smallest NCP value may be combined. In this manner, by recursively combining groups with the smallest NCP values, DA 102 may minimize information loss in the resultant anonymized data set 120.

As referenced above, top-down data anonymization techniques (e.g., K-anonymity and L-diversity) may result in information loss. With the top-down, the entire data set is taken as a single equivalence class, and then the groups with the highest NCP values are partitioned over and over again until partition cannot be further split and K or L are satisfied for each partition. However the high degrees or percentages of information loss that result may be problematic for some users or data sets.

A bottom-up approach may help minimize information loss that occurs as a result of data anonymization. In bottom-up, each tuple is regarded as its own equivalence class, and the tuples are combined until K or L 116 is satisfied. In a modified bottom-up approach (as shown in the example below), the data may be sorted and grouped based on an overlap of values (in K-anonymity) and then those groups may be combined. In an embodiment, the grouping may include splitting the input table 106 into a number of different groups based on the sort.

```
anonymize(Table, Quasi-Attributes, k){
    sort table based on quasi attributes;
    spilt table into groups(G) that each group contains tuples with distinct values on quasi attributes
    stores the groups having the number of tuples equal or greater than k into final equivalence class list (Final_Results) and remove such groups from groups G;
    for each group G_i in G {
        scan all other groups to find group G_j such that NCP(G_i ∪ G_j) is minimized;
        merge G_j into G_i;
        remove G_j from G;
        if (|G_i| >= k) {
            store merged group G_i into Final_Results;
            remove G_i from G;
        }
    }
    return Final_Results.
```

With bottom up, the groups with the smallest NCP values are identified and combined to produce the smallest NCP. This sort and combination may consume fewer resources than a traditional bottom-up approach and provide less information loss than a top-down approach.

The bottom-up approach consumes greater resources than top-down, but yields less information loss. As the size of the initial data set increases, so too does the gap or gains with information loss in top down v. bottom up.

With sufficiently small data sets, the resultant anonymized data 120 may be the same for both top-down and bottom-up. As such, with smaller data sets, below a particular or specified threshold, a user may only select top-down anonymization. But once the data size grows beyond the threshold, the resultant data set 120 using the bottom-up approach may vary from the resultant data set 120 using the top-down approach; the former having less information loss. A user may balance the need for efficient data anonymization with information loss concerns to determine or configure how DA 102 performs data anonymization.

Figure 3:
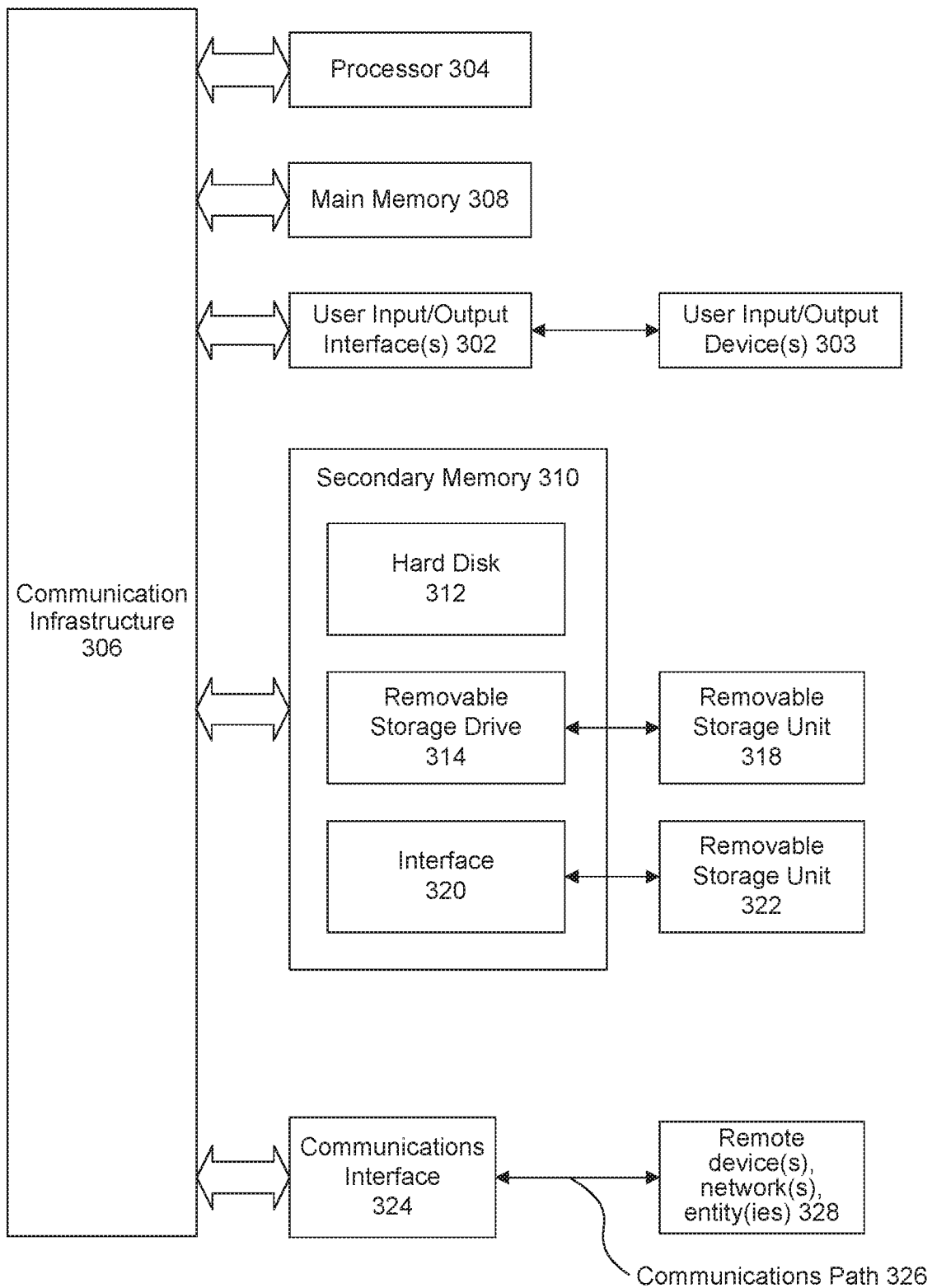
FIG. 3 is an example computer system useful for implementing various embodiments.

Various embodiments may be implemented, for example, using one or more well-known computer systems, such as computer system 300 shown in FIG. 3. One or more computer systems 300 may be used, for example, to implement any of the embodiments discussed herein, as well as combinations and sub-combinations thereof.

Computer system 300 may include one or more processors (also called central processing units, or CPUs), such as a processor 304. Processor 304 may be connected to a communication infrastructure or bus 306.

Computer system 300 may also include user input/output device(s) 303, such as monitors, keyboards, pointing devices, etc., which may communicate with communication infrastructure 306 through user input/output interface(s) 302.

One or more of processors 304 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 300 may also include a main or primary memory 308, such as random access memory (RAM). Main memory 308 may include one or more levels of cache. Main memory 308 may have stored therein control logic (i.e., computer software) and/or data.

Computer system 300 may also include one or more secondary storage devices or memory 310. Secondary memory 310 may include, for example, a hard disk drive 312 and/or a removable storage device or drive 314. Removable storage drive 314 may be a floppy disk drive, a magnetic tape drive, a compact disk drive, an optical storage device, tape backup device, and/or any other storage device/drive.

Removable storage drive 314 may interact with a removable storage unit 318. Removable storage unit 318 may include a computer usable or readable storage device having stored thereon computer software (control logic) and/or data. Removable storage unit 318 may be a floppy disk, magnetic tape, compact disk, DVD, optical storage disk, and/any other computer data storage device. Removable storage drive 314 may read from and/or write to removable storage unit 318.

Secondary memory 310 may include other means, devices, components, instrumentalities or other approaches for allowing computer programs and/or other instructions and/or data to be accessed by computer system 300. Such means, devices, components, instrumentalities or other approaches may include, for example, a removable storage unit 322 and an interface 320. Examples of the removable storage unit 322 and the interface 320 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 300 may further include a communication or network interface 324. Communication interface 324 may enable computer system 300 to communicate and interact with any combination of external devices, external networks, external entities, etc. (individually and collectively referenced by reference number 328). For example, communication interface 324 may allow computer system 300 to communicate with external or remote devices 328 over communications path 326, which may be wired and/or wireless (or a combination thereof), and which may include any combination of LANs, WANs, the Internet, etc. Control logic and/or data may be transmitted to and from computer system 300 via communication path 326.

Computer system 300 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 300 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 300 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 300, main memory 308, secondary memory 310, and removable storage units 318 and 322, as well as tangible articles of manufacture embodying any combination of the foregoing. Such control logic, when executed by one or more data processing devices (such as computer system 300), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 3. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A method comprising:
   receiving an indication to perform data anonymization based on one or more quasi attributes of a data set;
   wherein one or more hardware processors are configured to perform operations comprising sorting the data set based on the one or more quasi attributes, wherein the data set comprises a plurality of records including a value corresponding to each of the one or more quasi attributes;
   grouping the sorted data set into a first plurality of groups, wherein each group includes one or more of the records with a shared value on the one or more quasi attributes;
   identifying from amongst the first plurality of groups a particular group that does not include enough records to satisfy an anonymization threshold;
   identifying one group of the first plurality of groups that satisfies the anonymization threshold, wherein the identified group is not available for combination with the particular group;
   identifying a second group and a third group of the first plurality of groups that do not satisfy the anonymization threshold;
   determining which of the second group and the third group includes the smallest information loss; and
   wherein the one or more hardware processors are configured to perform operations comprising combining the particular group with the determined group, wherein the combined group satisfies the anonymization threshold and preserves a privacy of one or more parties associated with the data set that were identifiable prior to the combined group satisfying the anonymization threshold.

2. The method of claim 1, wherein the data anonymization is K-anonymity, and wherein the anonymization threshold indicates a minimum number of records to be included in each group.

3. The method of claim 1, wherein the combining comprises:
   identifying one group of the first plurality of groups that satisfies the anonymization threshold prior to the combining, wherein the identified group is not available for combination with the particular group.

4. The method of claim 3, wherein the combining comprises:
   identifying a second group of the first plurality of groups that does not satisfy the anonymization threshold prior to the combining; and
   combining the particular group with the second group.

5. The method of claim 1, further comprising:
   providing an anonymized data set including each of the first plurality of groups, and including one or more combined groups, wherein each of the first plurality of groups and the one or more combined groups satisfies the anonymization threshold.

6. The method of claim 1, wherein the data anonymization is L-diversity.

7. A system, comprising:
   a memory; and
   at least one processor coupled to the memory and configured to:
   receive an indication to perform data anonymization based on one or more quasi attributes of a data set;
   sort the data set based on the one or more quasi attributes, wherein the data set comprises a plurality of records including a value corresponding to each of the one or more quasi attributes;
   group the sorted data set into a first plurality of groups, wherein each group includes one or more of the records with a shared value on the one or more quasi attributes;
   identify from amongst the first plurality of groups a particular group that does not include enough records to satisfy an anonymization threshold;
   identify one group of the first plurality of groups that satisfies the anonymization threshold, wherein the identified group is not available for combination with the particular group;
   identify a second group and a third group of the first plurality of groups that do not satisfy the anonymization threshold;
   determine which of the second group and the third group includes the smallest information loss; and
   combine the particular group with the determined group, wherein the combined group satisfies the anonymization threshold and preserves a privacy of one or more parties associated with the data set that were identifiable prior to the combined group satisfying the anonymization threshold.

8. The system of claim 7, wherein the data anonymization is K-anonymity, and wherein the anonymization threshold indicates a minimum number of records to be included in each group.

9. The system of claim 7, wherein the processor that combines is configured to:
   identify one group of the first plurality of groups that satisfies the anonymization threshold prior to the combining, wherein the identified group is not available for combination with the particular group.

10. The system of claim 9, wherein the processor that combines is configured to:
    identify a second group of the first plurality of groups that does not satisfy the anonymization threshold prior to the combining; and
    combine the particular group with the second group.

11. The system of claim 7, wherein the processor is further configured to:
    provide an anonymized data set including each of the first plurality of groups, and including one or more combined groups, wherein each of the first plurality of groups and the one or more combined groups satisfy the anonymization threshold.

12. The system of claim 7, wherein the data anonymization is L-diversity.

13. A non-transitory computer-readable device having instructions stored thereon that, when executed by at least one computing device, causes the at least one computing device to perform operations comprising:
    receiving an indication to perform data anonymization based on one or more quasi attributes of a data set;

sorting the data set based on the one or more quasi attributes, wherein the data set comprises a plurality of records including a value corresponding to each of the one or more quasi attributes;

grouping the sorted data set into a first plurality of groups, wherein each group includes one or more of the records with a shared value on the one or more quasi attributes;

identifying from amongst the first plurality of groups a particular group that does not include enough records to satisfy an anonymization threshold;

identifying one group of the first plurality of groups that satisfies the anonymization threshold, wherein the identified group is not available for combination with the particular group;

identifying a second group and a third group of the first plurality of groups that do not satisfy the anonymization threshold;

determining which of the second group and the third group includes the smallest information loss; and combining the particular group with the determined group, wherein the combined group satisfies the anonymization threshold and preserves a privacy of one or more parties associated with the data set that were identifiable prior to the combined group satisfying the anonymization threshold.

14. The non-transitory computer-readable device of claim 13, wherein the data anonymization is K-anonymity, and wherein the anonymization threshold indicates a minimum number of records to be included in each group.

15. The non-transitory computer-readable device of claim 13, wherein the at least one computing device that combines is configured to perform operations comprising:

identifying one group of the first plurality of groups that satisfies the anonymization threshold prior to the combining, wherein the identified group is not available for combination with the particular group.

16. The non-transitory computer-readable device of claim 15, wherein the at least one computing device that combines is configured to perform operations comprising:

identifying a second group of the first plurality of groups that does not satisfy the anonymization threshold prior to the combining; and combining the particular group with the second group.

17. The non-transitory computer-readable device of claim 13, wherein the data anonymization is L-diversity.

* * * * *